United States Patent [19]

Suh

[11] 3,997,608
[45] Dec. 14, 1976

[54] N-SUBSTITUTED-DIHYDROXYPHENE-THYLAMINES

[75] Inventor: John T. Suh, Mequon, Wis.

[73] Assignee: Richardson-Merrell Inc., Wilton, Conn.

[22] Filed: Feb. 5, 1975

[21] Appl. No.: 547,214

Related U.S. Application Data

[63] Continuation-in-part of Ser. No. 376,686, July 5, 1973, Pat. No. 3,894,051.

[52] U.S. Cl. .................... 260/570.8 R; 260/459 R; 260/465 F; 260/465 K; 260/501.18; 260/566 F; 260/567.6 M; 260/592; 424/316; 424/330
[51] Int. Cl.$^2$ ........................................ C07C 87/28
[58] Field of Search .................. 260/570.8, 501.18

[56] References Cited
UNITED STATES PATENTS 3,894,051  8/1975  Suh ............................. 260/570.8 X

*Primary Examiner*—Robert V. Hines
*Attorney, Agent, or Firm*—L. Ruth Hattan; Eugene O. Retter; George W. Rauchfuss, Jr.

[57] ABSTRACT

The compounds are N-substituted-dihydroxyphenethylamines which are cardiotonic agents, central nervous system depressants and analgetic agents. Representative of the compounds disclosed is N-(3,4-dihydroxyphenisobutyl)-β-isopropyl-3,4-dihydroxyphenethylamine.

7 Claims, No Drawings

N-SUBSTITUTED-DIHYDROXYPHENETHYLA-MINES

RELATED CASE

This application is a continuation-in-part of our co-pending application, U.S. Ser. No. 376,686, filed July 5, 1973 and now U.S. Pat. No. 3,894,051.

BACKGROUND OF THE INVENTION

α-(3,4-Dihydroxyphenyl)-β-(N-3',4'-methylenedioxyphenyl)-alkylamino ethanols are disclosed in U.S. Pat. No. 3,139,441, and 1-(4'-hydroxy-3'-(hydroxymethyl)-phenyl)-1-hydroxy-2-aralkylaminoethanes are disclosed in U.S. Pat. No. 3,700,692.

DETAILED DESCRIPTION

The compounds of the present invention may be represented by the following formula:

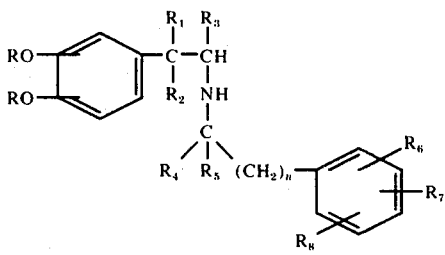

in which R is hydrogen, an alkyl of 1 to 4 carbon atoms or benzyl, $R_1$ is a straight chain alkyl of 1 to 7 carbon atoms, a branched chain alkyl of 3 to 7 carbon atoms, such as isopropyl, s-butyl or t-butyl, or a cycloalkyl of 3 to 7 carbon atoms such as cyclopropyl or cyclobutyl, $R_2$, $R_3$ and $R_4$ are hydrogen or lower alkyl of 1 to 4 carbon atoms, $R_5$ is a lower alkyl of 1 to 4 carbon atoms, $R_6$, $R_7$ and $R_8$ are hydroxy, lower alkoxy of 1 to 4 carbon atoms, a halogen such as chloro, bromo or fluoro, trifluoromethyl, and n is 1, 2 or 3.

The preferred method of preparing the compounds is illustrated by the following, which is a description of the preparation of N-(3,4-dihydroxyphenisobutyl)-β-isopropyl-3,4-dihydroxyphenethylamine. A solution containing 2-(3,4-dibenzyloxyphenyl)-isopropylamine and 4-(3,4-dimethoxyphenyl)-butan-2-one in anhydrous benzene is heated at reflux for about four hours, at which time the solution is concentrated. The thus obtained product is dissolved in methanol and treated with sodium borohydride to yield the compound N-(3,4-dibenzyloxyphenisobutyl)-β-isopropyl-3,4-dibenzyloxyphenethylamine. The thus obtained dibenzyloxy derivative is then hydrogenated in the presence of a suitable catalyst such as 5% palladium on carbon to form the desired amine. A similar process may be employed utilizing different appropriate amines and aldehydes or ketones to produce other compounds falling within the scope of the invention.

The preferred process of preparing the compounds may be illustrated as follows:

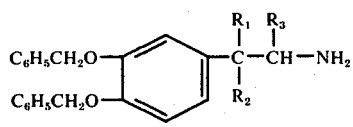

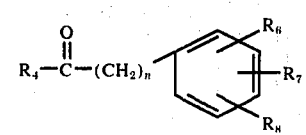

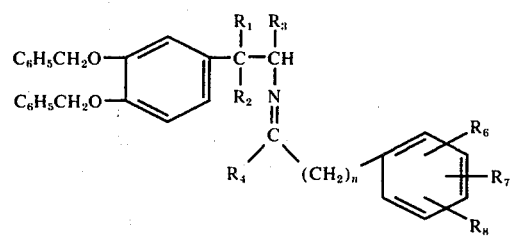

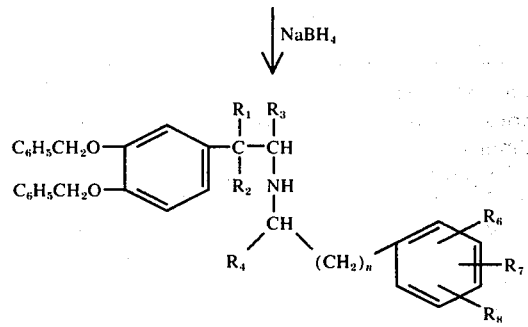

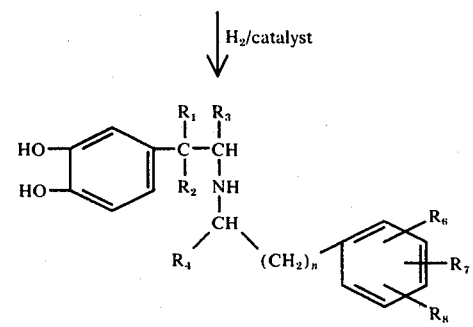

in which all symbols are as previously defined.

Among the compounds that may be prepared by the described process are the following:

N-(3,4,5-trimethoxyphenisobutyl)-β-(isopropyl)-3,4-dihydroxyphenethylamine,

N-(α,α-dimethyl-3,4-dimethoxyphenpropyl)-β-(isopropyl)-3,4-dihydroxyphenethylamine, N-(3,4-dichlorophenisobutyl)-β-(isopropyl)-3,4-dihydroxyphenethylamine, N-(4-trifluoromethylphenisobutyl)-β-(isopropyl)-3,4-dihydroxyphenethylamine, N-(4-hydroxyphenisobutyl)-β-(isopropyl)-3,4-dihydroxyphenethylamine, N-(3,4-dihydroxyphenisobutyl)-β-(isopropyl)-3,4-dihydroxyphenethylamine, N-(4-fluorophenisobutyl)-β-(isopropyl)-3,4-dibenzyloxyphenethylamine, and ;

N-(3,4-dimethoxyphenisobutyl)-β-(t-butyl)-3,4-dimethoxyphenethylamine.

The novel compounds of the present invention are useful as pharmaceutical agents because of their central nervous system depressant activity, their analgetic activity and their cardiotonic activity. The compounds are especially interesting as cardiotonic agents or for the treatment of shock. For example, in tests involving dogs, the compound N-(3,4-dihydroxyphenisobutyl)-β-isopropyl-3,4-dihydroxyphen ethylamine was found, when administered intravenously at a dose of 0.3 mg/kg, to increase the contractile force of the heart.

Acid addition salts of the compounds of the present invention may be conveniently prepared by contacting the compounds which are capable of forming such salts with a suitable acid such as formic acid, citric acid, maleic acid, sulfuric acid, hydrochloric acid, succinic acid, tartaric acid, benzoic acid or fumaric acid.

Quaternary ammonium salts may be formed by contacting the salt-forming compounds with a suitable alkylating agent such as dimethyl sulfate, or an alkyl halide such as methyl chloride, methyl iodide or ethyl bromide.

When intended for use as pharmaceutical agents, the compounds are preferably combined with a major amount of one or more suitable pharmaceutical diluents and formed into unit dosage forms. Such dosage forms provide suitable means for oral and parenteral administration.

The pharmaceutical diluents which may be employed may be either liquid or solid, but the preferred liquid carrier is water. In the event the compounds are not soluble in water, a pharmaceutically acceptable organic solvent such as propylene glycol may be employed.

Solid pharmaceutical diluents such as starch, sugar and talc can be utilized to form powders which can in turn be used as such or may be tableted or encapsulated. In addition to the forementioned material, a wide variety of conventional pharmaceutical lubricants, disintegrating agents, flavoring agents and the like may also be employed.

The unit dosage forms may contain a concentration of 0.1% to 10% or more by weight of one or more of the novel compounds. Generally, such dosage forms will contain about 5 to 250 mg. of the active ingredients. One or more of such dosage forms may be administered daily. In actual practice, the amount of drug required to produce the desired effect will, of course, vary considerably because of patient differences.

The following examples are presented to illustrate this invention:

EXAMPLE 1

α-iso-Propylidene-3,4-dimethoxyphenyl-acetonitrile

To a solution of 12.54 g. (0.545 mole) of sodium in 900 ml. of ethanol is added 118 g. (0.632 mole) of 3,4-dimethoxyphenyl-acetonitrile in 5 minutes. The solution is heated to reflux in 0.25 hour and maintained 0.75 hour. It is then cooled to 22°, after which 106 ml. (1.45 moles) of acetone is added in 0.25 hour. The solution is stirred at 22° for 0.5 hour, heated to reflux in 0.5 hour, and maintained 4 hours. The solution is then diluted to 3.3 liters with water and extracted three times with ether. The combined extracts are washed successively with water and brine, dried and concentrated to yield an oil which is fractionated through a 6 inches 24/40 column to yield 76.1 g. of an oil which crystallizes, b.p. 135°–160°/0.3 mm. The material is recrystallized from 330 ml. of ethanol to yield 48.9 g. (41.3%) of α-iso-propylidene3,4-dimethoxyphenyl-acetonitrile as white needles in two crops, 46.0 g., m.p. 95°–98°; 2.9 g., m.p. 93°–95°.

EXAMPLE 2

α-iso-Propyl-3,4-dimethoxyphenylacetonitrile

To a solution of 21.7 g. (0.1 mole) of α-iso-propylidene-3,4-dimethoxyphenylacetonitrile in 280 ml. of ethanol is added 0.75 g. of 10% palladium on carbon, and the mixture is shaken with hydrogen (43.3 psi) until the theoretical amount of hydrogen (8.2 psi) has been taken up in 5 hours. The catalyst is removed by filtration and the filtrate reduced in vacuo to yield a clear syrup which crystallizes upon standing. It is recrystallized from ethanol to yield 18.3 g. (84%) of α-iso-propyl-3,4-dimethoxyphenylacetonitrile as a white crystalline solid, m.p. 45.5°–49°.

Anal. Calcd. for $C_{13}H_{17}NO_2$: C, 71.18; H, 7.83; N, 6.39. Found: C, 71.13; H, 7.73; N, 16.53.

EXAMPLE 3

α-iso-Propyl-3,4-dihydroxyphenylacetonitrile

A mixture of 13.9 g. (0.06 mole) of α-iso-propyl-3,4-dimethoxyphenylacetonitrile, and 43.7 g. (0.38 mole) of pyridine hydrochloride is heated in an oil bath for 3.5 hours at 200°–220°. The clear solution is poured into 900 ml. of water, cooled, and the resulting solid collected and recrystallized from 40% isopropanol to yield 9.4g. of α-iso-propyl-3,4-dihydroxyphenylacetonitrile as a light brown crystalline solid, m.p. 134.5°–136°.

EXAMPLE 4

α-iso-Propyl-3,4-dibenzyloxyphenylacetonitrile

A mixture of 27.6 g. (0.144 mole) of α-iso-propyl-3,4- dihydroxyphenylacetonitrile, 41.3 ml. (0.456 mole) of α-chlorotoluene, and 56.1 g. (0.406 mole) of potassium carbonate in 305 ml. of ethanol is refluxed for five hours. The mixture is then filtered while still hot. The filtrate is cooled, and the precipitated solid collected and washed with cold ethanol and then water. It is then dried to yield 46.7 g. of α-iso-propyl-3,4-dibenzyloxyphenylacetonitrile as a white solid, m.p. 75°–76°.

EXAMPLE 5

3,4-Dibenzyloxy-β-isopropylphenethylamine Hydrochloride

To 54 ml. (0.054 mole) of borane/tetrahydrofuran is added a solution of 20.0 g. (0.054 mole) of α-isopropyl3,4-dibenzyloxyphenylacetonitrile in 53 ml. of tetrahydrofuran in ten minutes while cooling the reaction in a cold water bath. The solution is then stirred at 22° for 22 hours, cooled and 25 ml. of ethanol added in five minutes, and the solution then stirred 0.25 hour at 22°. The solution is then concentrated to a residual oil, and a solution of 6.55 g. (0.164 mole) of NaOH in 27 ml. of water added, heated to reflux in 0.5 hour and maintained for 1 hour. The mixture is cooled, diluted with water and extracted twice with ether. The combined extracts are washed twice with brine, dried and concentrated to yield a brown oil which is distilled through a stillhead to yield 9.2 g. of a light yellow oil. The material is dissolved in ether, acidified with ethereal HCl and diluted with n-heptane. The precipitated solid is collected and recrystallized from ethanol to yield 2.8 g. of 3,4-dibenzyloxy-β-isopropylphenethylamine hydrochloride as a white solid, m.p. 151.5°–153°.

EXAMPLE 6

N-(3,4-Dibenzyloxyphenisobutyl)-62-isopropyl-3,4-dibenzyloxyphenethylamine

In 150 ml. benzene is dissolved 2.76 g. (0.00736 mole) of 3,4-dibenzyloxy-β-isopropylphenethylamine and 2.65 g. (0.00736 mole) of 4-[3,4-(dibenzyloxy)-phenyl]-butan-2-one. The solution is refluxed with a water collector for 63 hours and the solvent evaporated to give an oily Schiff's base. The Schiff's base is dissolved in 100 ml. ethanol, chilled, and 0.6 g. (0.0158 mole) sodium borohydride added as a dry powder. The mixture is stirred at room temperature for one hour and the solvent evaporated. The residue is dissolved in ether, washed with water and dried. Evaporation of the solvent gives 5.15 g. yellow oil. Chromatography over 150 g. silica gel (ether:hexane, 1:1) affords N-(3,4-dibenzyloxyphenisobutyl)-β-isopropyl-3,4-dibenzyloxyphenethylamine as a colorless oil.

EXAMPLE 7

N-(3,4-Dihydroxyphenisobutyl)-β-isopropyl-3,4-dihydroxyphenethylamine

To 0.3 g. of a 5% palladium on carbon catalyst is added 2.01 g. (0.0028 mole) of N-(3,4-dibenzyloxyphenisobutyl)-β-isopropyl-3,4-dibenzyloxyphenethylamine in 50 ml. absolute ethanol. Hydrogenation at atmospheric pressure is continued until four equivalents of gas are taken up. The mixture is acidified with ethereal-HCl and filtered. The solvent is evaporated and the residue dried und high vacuum followed by trituration with hexane to give N-(3,4-dihydroxyphenisobutyl)-β-isopropyl-3,4-dihydroxyphenethylamine as an amorphous solid, m.p. 85°.

Anal. Calcd. for $C_{21}H_{30}NO_4Cl \cdot H_2O$: C, 60.93; H, 7.79; N, 3.38. Found: C, 60.79; H, 7.83; N, 3.28.

EXAMPLE 8

N-(3,4-Dimethoxyphenylisobutyl)-62-(isopropyl)-3,4-dibenzyloxyphenethylamine A mixture of 16.5 g. (0.044 mole) of 2-(3,4-dibenzyloxyphenyl)-isopropylamine and 9.2 g. (0.044 mole) of 4-(3,4-dimethoxyphenyl)-butan-2-one in 250 cc. benzene is refluxed four hours allowing the water to distill off. The solvent is removed and the residue dissolved in 250 cc. methyl alcohol and 1.7 g. (0.044 mole) of sodium borohydride added. The mixture is stirred at 21° overnight. The system is cooled, acetone added and the solvent evaporated. The residue is dissolved in chloroform, washed with water, saturated brine and dried over $Na_2SO_4$. Removal of the solvent leaves a viscous oil which is chromatographed over 200 g. of silica gel (benzenehexane) to afford 4.4 g. of N-(3,4-dimethoxyphenylisobutyl)-β-(isopropyl)-3,4-dibenzyloxyphenethylamine as an off-white oil.

EXAMPLE 9

N-(3,4-Dimethoxyphenylisobutyl)-β-(isopropyl)-3,4dihydroxyphenethylamine Hydrochloride Hydrate A mixture of 5.1 g. (0.09 mole) of N-(3,4-dimethoxyphenylisobutyl)-β-(isopropyl)-3,4-dibenzyloxyphenethylamine and 1.0 g. of 5% Pd/C in 100 cc. of ethyl alcohol is shaken under 40 psi of hydrogen for four hours (1.4 psi absorbed). The reaction mixture is filtered and acidified with ethereal HCl. The reaction mixture is then concentrated to yield a white glass which is dissolved in 35 ml. of water, treated with Darco, filtered, and concentrated at below 55°. The flask is immersed in a water bath and heated at 50°–72° for three hours at 0.5 mm. to yield 2.29 g. of N-(3,4-dimethoxyphenylisobutyl)-β-(isopropyl)-3,4-dihydroxyphenethylamine hydrochloride hydrate as a brown glass, m.p. 73°–77° (d.).

I claim:
1. A compound of the formula:

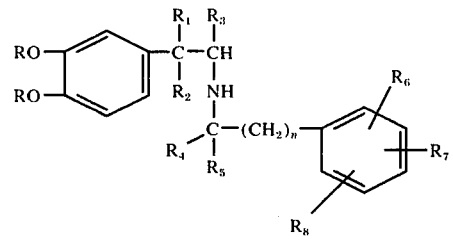

in which R is hydrogen, an alkyl of 1 to 4 carbon atoms or benzyl, $R_1$ is a straight chain alkyl of 1 to 7 carbon atoms, a branched chain alkyl of 3 to 7 carbon atoms, or a cycloalkyl of 3 to 7 carbon atoms, $R_2$, $R_3$ and $R_4$ are hydrogen or lower alkyl of 1 to 4 carbon atoms, $R_5$ is a lower alkyl of 1 to 4 carbon atoms, $R_6$, $R_7$ and $R_8$ are hydroxy, lower alkoxy of 1 to 4 carbon atoms, chloro, bromo or fluoro, or trifluoromethyl, and n is 1 or 2.

2. A compound of claim 1 in which R is hydrogen.
3. A compound of claim 1 in which R is benzyl.
4. A compound of claim 1 in which $R_4$ is methyl.
5. A compound of claim 1 in which $R_1$ is isopropyl.
6. The compound of claim 1 which is N-(3,4-dihydroxyphenisobutyl)-β-isopropyl-3,4-dihydroxyphenethylamine.
7. The compound of claim 1 which is N-(3,4-dimethoxyphenylisobutyl)-β-(isopropyl)-3,4-dihydroxyphenethylamine hydrochloride hydrate.

* * * * *

UNITED STATES PATENT AND TRADEMARK OFFICE
CERTIFICATE OF CORRECTION

PATENT NO. : 3,997,608
DATED : December 14, 1976
INVENTOR(S) : John T. Suh

It is certified that error appears in the above-identified patent and that said Letters Patent are hereby corrected as shown below:

Column 5, line 35, "und" should read "under";
line 43, "........butyl)-62" should read
"........butyl)-β-".

Signed and Sealed this

Twenty-second Day of March 1977

[SEAL]

Attest:

RUTH C. MASON
Attesting Officer

C. MARSHALL DANN
Commissioner of Patents and Trademarks